United States Patent [19]
Nietuspki et al.

[11] Patent Number: 5,582,974
[45] Date of Patent: Dec. 10, 1996

[54] NUCLEIC ACID PROBES FOR THE DETECTION OF STAPHYLOCOCCUS AUREUS

[75] Inventors: Raymond M. Nietuspki, Millbury, Mass.; Jyotsna Shah, Nashua, N.H.; David J. Lane, Milford, Mass.

[73] Assignee: Amoco Corporation, Chicago, Ill.

[21] Appl. No.: 171,864

[22] Filed: Dec. 22, 1993

Related U.S. Application Data

[63] Continuation of Ser. No. 867,276, Apr. 9, 1992, abandoned, which is a continuation of Ser. No. 356,036, May 23, 1989, abandoned.

[51] Int. Cl.⁶ .............................. C12Q 1/68; C07H 21/00
[52] U.S. Cl. ............................... 435/6; 536/24.32
[58] Field of Search .................. 435/6; 536/23.1, 536/24.1, 24.3, 24.32

[56] References Cited

U.S. PATENT DOCUMENTS

| | | | |
|---|---|---|---|
| 4,358,535 | 11/1982 | Falkow et al. | |
| 4,717,653 | 6/1988 | Webster | 435/6 |
| 4,851,330 | 7/1989 | Kohne | 435/6 |

FOREIGN PATENT DOCUMENTS

| | | | |
|---|---|---|---|
| 0272009 | 6/1988 | European Pat. Off. | |
| 88/03957 | 6/1988 | WIPO | 435/6 |

OTHER PUBLICATIONS

Flowers et al., J of Bacterol., vol. 141, No. 2, pp. 645–651 (1980).
Edmar et al, Nature, v. 334, Aug. 11, 1988, pp. 519–522.
Shinozaki et al, Embo J, v. 5, pp. 2043–49 (1986).
*Bergey's Manual of Systematic Bateriology*, P. H. A. Sneath, ed., pp. 1015–1019, (1986).
*FDA/BAM Bateriological Analytical Manual*, Association of Official Analytical Chemists, 6th ed. (1984).
Fox et al., *Int. J. Systematic Bacteriol.*, 27:44–57 (1977).
Kohne et al., *Biophysical Journal*, 8:1104–1118 (1968).
Liebl et al., *FEMS Microbiology Letters*, 44:179–184 (1987).
Notermans et al., "Synthetic Enterotoxin B DNA Probes for Detection of Enterotoxigenic Staphylococcusaureus Strains", *Applied and Environmental Microbiology*, 54:531–533 (1988).
Pace et al., *J. Bacteriol.*, 107:543–547 (1971).
Sogin et al., *J. Molecular Evolution*, 1:173–184 (1972).
Liebl et al., "Use of Staphylococcal nuclease gene as DNA PNbc for S. aureus", *FEMS Microbiology Letters*, vol. 44 (1987) 179–184.

*Primary Examiner*—George C. Elliott
*Attorney, Agent, or Firm*—Norval B. Galloway

[57] ABSTRACT

Nucleic acid probes capable of hybridizing to rRNA of *Staphylococcus aureus* and not to rRNA of non-*Staphylococcus aureus* are described along with methods utilizing such probes for the detection of *Staphylococcus aureus* in food and other samples.

15 Claims, No Drawings

5,582,974

NUCLEIC ACID PROBES FOR THE DETECTION OF STAPHYLOCOCCUS AUREUS

This is a continuation of application Ser. No. 867,276, filed Apr. 9, 1992, now abandoned, which is a continuation of application Ser. No. 07/356,036, filed May 23, 1989, now abandoned.

FIELD OF THE INVENTION

This invention relates to detecting bacteria belonging to the species *Staphylococcus aureus* and more specifically provides nucleic acid probes and compositions along with methods for their use for the specific detection of *Staphylococcus aureus*.

BACKGROUND OF THE INVENTION

The term *"Staphylococcus aureus"* as used herein, refers to bacteria classified as such in Bergey's Manual of Systematic Bacteriology (P. H. A. Sneath, ed., 1986, PP. 1015–1019, Williams & Wilkins). Detection of *Staphylococcus aureus* is important in various medical and public health contexts. In particular, *Staphylococcus aureus* can cause severe food poisoning. Thousands of cases of food poisoning are reported in the United States each year. Many more unreported cases are suspected. Foods are examined for the presence of *S. aureus* and/or its enterotoxins to confirm that *S. aureus* is the causative agent of foodborne illness, to determine whether a food is a potential source of "staph" food poisoning, and to demonstrate post-processing contamination, which generally is due to human contact or contaminated food-contact surfaces.

Methods for detecting and enumerating *Staphylococcus aureus* depend to some extent on the reasons for testing the food and on the past history of the test material itself. The methods of analysis for *S. aureus* which are most commonly used (and which provide the type of information required by the Food and Drug Administration) are given in Chapters 14 and 15 of the FDA/BAM Bacteriological Analytical Manual (6th edition, 1984, Association of Official Analytical Chemists). Generally, such methods involve the isolation of *Staphylococcus aureus* from an appropriately prepared sample on microbiological medium under conditions favorable for growth of these bacteria. The resulting colonies then typically are examined for morphological and biochemical characteristics, a process that generally is initiated 48 hours after acquisition of the sample and disadvantageously takes between four to six days to complete. Therefore, it is an aspect of the present invention to provide nucleic acid probes which are specific for *Staphylococcus aureus* and which do not react with other bacteria or fungi which may be present in sampled materials. Such probes may be used in a variety of assay systems which avoid many of the disadvantages associated with traditional, multi-day culturing techniques.

It is another aspect of the present invention to provide probes which can hybridize to target regions which can be rendered accessible to probes under normal assay conditions.

While Kohne et al. (Biophysical Journal 8:1104–1118, 1968) discuss one method for preparing probes to rRNA sequences, they do not provide the teaching necessary to make *Staphylococcus aureus* specific probes.

Pace and Campbell (Journal of Bacteriology 107:543–547, 1971) discuss the homology of ribosomal ribonucleic acids from diverse bacterial species and a hybridization method for quantifying such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to prokaryotic systematics. These references, however, fail to relieve the deficiency of Kohne's teaching with respect to *Staphylococcus aureus* and in particular, do not provide *Staphylococcus aureus* specific probes useful in assays for detecting *Staphylococcus aureus* in food and other samples.

Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, at least in *E. coli,* are referred to as 5S, 16S and 23S rRNAs. These names historically are related to the size of the RNA molecules, as determined by their sedimentation rate. In actuality, however, ribosomal RNA molecules vary substantially in size between organisms. Nonetheless, 5S, 16S, and 23S rRNA are commonly used as generic names for the homologous RNA molecules in any bacteria, and this convention will be continued herein.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially, see below—Hybridization) to target nucleic acid sequences. In addition to their hybridization properties, probes also may contain certain constituents that pertain to their proper or optimal functioning under particular assay conditions. For example, probes may be modified to carry detection ligands (e.g. fluorescien, 32-P, biotin, etc.), or to facilitate their capture onto a solid support (e.g., poly-deoxyadenosine "tails"). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion to form a double-stranded nucleic acid with specific and stable hydrogen bonds.

The stringency of a particular set of hybridization conditions is defined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar.

SUMMARY OF THE INVENTION

In accordance with the various principles and aspects of the present invention, there are provided nucleic acid probes and probe sets comprising DNA or RNA sequences which hybridize, under specific conditions, to the ribosomal RNA molecules (rRNA) or rRNA genes (rDNA) of *Staphylococcus aureus* but which do not hybridize, under the same conditions, to the rRNA or rDNA of other related bacteria which may be present in test samples. Therefore the probe(s) of the present invention provide the basis for development of a valuable nucleic acid hybridization assay for the specific detection of *S. aureus* in food, clinical or environmental samples.

In our experience such nucleic acid hybridization based assays have been discovered to impart enhanced performance capabilities with respect to most currently available, microbiological methods for detection of bacteria in test samples, generally including:

a) increased sensitivity; i.e., the ability to detect said bacteria in a given sample more frequently;

b) potentially significant reductions in assay cost due to the use of inexpensive reagents and reduced labor;

c) accurate identification of even biochemically unusual strains of the target bacteria;

d) faster results because such tests do not require the isolation of the target bacterium from the sample prior to testing.

It has been discovered that other advantages incurred by directing the probes of the present invention against rRNA include the fact that the rRNAs detected constitute a significant component of cellular mass. Although estimates of cellular ribosome content vary, actively growing *Staphylococcus aureus* may contain upwards of 50,000 ribosomes per cell, and therefore 50,000 copies of each of the rRNAs (present in a 1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to *Staphylococcus aureus* rRNA target sequences which are sufficiently similar in all *Staphylococcus aureus* strains tested that they can hybridize to the target region in all such *Staphylococcus aureus*. Advantageously, these same rRNA target sequences are sufficiently different in most non-*Staphylococcus aureus* rRNAs that, under conditions where one of the probes, probe 1337, hybridizes to *S. aureus* rRNAs, it does not hybridize to most non-*S. aureus* rRNAs. These probe characteristics are defined as inclusivity and exclusivity, respectively.

The other preferred probe of the present invention, probe 1336, is as fully inclusive for *S. aureus* strains as probe 1337 and, in addition, probe 1336 also hybridizes to a few close relatives of *S. aureus*.

The discovery that probes could be generated with the extraordinary inclusivity and exclusivity characteristics of those of the present invention with respect to *S. aureus* was unpredictable and unexpected.

BRIEF DESCRIPTION OF THE TABLES

Further understanding of the principles and aspects of the present invention may be made by reference to the tables wherein:

Table 1—Shows alignment of the nucleotide sequences of the preferred probes of the present invention with the target nucleotide sequences of a number of Staphylococcus strains. The corresponding portions of the 23S rRNAs from a number of closely related non-*Staphylococcus aureus* bacteria also are shown for comparison. RNA (target) sequences are written 5' to 3', probe sequences are DNA and written 3' to 5'. Probes are shown along with the "core" region of variation upon which their inclusivity and exclusivity behavior are based. The lower case C (c) in probe 1336 indicates a modified cytosine residue to which a reporter group may or may not be attached depending on the assay format employed.

Table 2—Exemplifies the inclusivity and exclusivity behavior of the preferred probes toward a representative sampling of *Staphylococcus aureus* and non-*Staphylococcus aureus* strains in a dot blot hybridization assay.

DETAILED DESCRIPTION OF THE INVENTION AND BEST MODE

Probe Development Strategy

The first step taken in the development of the probes of the present invention involved identification of regions of 16S and 23S rRNA which potentially could serve as target sites for *Staphylococcus aureus* specific nucleic acid probes. As a practical matter, it is difficult to predict, a priori, which non-*Staphylococcus aureus* organisms might be present in any test sample.

Because of the large number of such potential non-*Staphylococcus aureus* bacteria, demonstrating exclusivity for any given probe sequence is not only unpredictable but also extremely difficult and laborious. A more rigorous criterion was adopted to obviate the need to know what non-*Staphylococcus aureus* bacteria might be present in all test samples that ultimately will be screened using the probes.

This entailed knowledge of the phylogenetic relationships among *Staphylococcus aureus* and between *Staphylococcus aureus* and other groups of bacteria.

Specifically, an operating but previously unproven hypothesis was adopted that the exclusivity criterion could be satisfied by determining that if a particular target region in *Staphylococcus aureus* rRNA could be identified which was sufficiently different from the homologous region in the rRNA of representative yet close evolutionary relatives of *Staphylococcus aureus*, then a probe to such a sequence could be used to distinguish between *Staphylococcus aureus* and the relatives by hybridization assay. Based on phylogenetic observations, it then was extrapolated that rRNA sequences of more distantly related organisms, even though their actual identity may not necessarily be known, should predictably be different in the aforementioned target region of sequence than the aforementioned close evolutionary relative of *Staphylococcus aureus*. However, it cannot be predicted, a priori, whether such regions exist or if they do, where within the rRNA such regions will be located.

As the first step in identifying regions of *Staphylococcus aureus* rRNA which could potentially serve as useful target sites for nucleic acid hybridization probes, nearly complete nucleotide sequences of the 16S and 23S rRNAs from a number of strains of *Staphylococcus aureus* were determined.

The nucleotide sequences were determined by standard laboratory protocols either by cloning (Maniatis et al., 1982, Molecular Cloning; A Laboratory Manual, Cold Spring Harbor Laboratory, New York, pp 545) and sequencing (Maxam and Gilbert, 1977, Proceedings of the National Academy of Science, USA 74:560–564: Sanger et al., 1977, Proceedings of the National Academy of Science, USA 74:5463–5467) the genes which specify the rRNAs, and/or by direct sequencing of the rRNAs themselves using reverse transcriptase (Lane et al., 1985, Proceedings of the National Academy of Science, USA 82:6955–6959).

The determined *Staphylococcus aureus* rRNA nucleotide sequences were compared to other available rRNA nucleotide sequences, in particular to those of closely related bacteria such as other species of Staphylococcus, Streptococcus, Enterococcus, Listeria, and Bacillus etc. which also were determined as part of this work.

Comparison of the sequences of *Staphylococcus aureus* and its very close relative *Staphylococcus epidermidis* proved especially valuable. One region of sequence was identified which appeared to be different in the two species of Staphylococcus and between *Staphylococcus aureus* and non-Staphylococcus bacteria. Table 1 shows a detailed comparison of this region in a variety of Staphylococcus and non-Staphylococcus bacteria. Finally, the utility of probes based on these observed nucleotide sequence differences subsequently was confirmed by extensive hybridization testing and is shown in Table 2.

Physical Description of the Probes

The foregoing probe selection strategy yielded a number of probes useful for identifying *Staphylococcus aureus* bacteria in samples. The following preferred oligonucleotide probes are disclosed herein:

Probe 1336:
5'-cGATTATTACCTTCTTTGATTCATCTTTCCAGAcT-3'
Probe 1337:
5'-ATTCGTCTAATGTCCTCCTTTGTAACTC-3'

Probes 1336 and 1337 are targeted at adjacent regions of the 23S rRNA (Table 1). Probe 1336 is targeted at the region of *Staphylococcus aureus* 23S rRNA corresponding approximately to nucleotide positions 304 to 335 (using the *E. coli* numbering system) and probe 1337 is targeted at positions ca. 274 to 301 (Table 1).

As indicated in Table 1, probe 1337 is "built" around the positions of core variation which are most useful for discriminating between *Staphylococcus aureus* and its very close relative, *Staphylococcus epidermidis*. The core sequence, GGACGACA, in the 23S rRNA of *Staphylococcus aureus* contains 5 sequence differences with respect to the homologous region of *Staphylococcus epidermidis* (indicated by the upper case letters in the core sequence shown in Table 1).

Probe 1336 will not discriminate between *Staphylococcus aureus* and *Staphylococcus epidermidis*—based on the discovered identity of the target sequences for this probe in these two bacterial 23S rRNAs (Table 1). Therefore, probe 1336 would not be as useful, on its own, as a *Staphylococcus aureus*-specific probe since discrimination between these two bacteria generally is considered important for most potential applications of an assay which would employ such probes. However, probe 1336 does have important and novel specificity properties. The core region of variation defined for probe 1336 is a concentration of sequence differences between *Staphylococcus aureus* (and *S. epidermidis*) and *Staphylococcus carnosis*. From the sequence data, probe 1336 therefore may define a taxonomically higher-level group of *Staphylococcus aureus* relatives than probe 1337. This was confirmed by the hybridization data shown in Table 2.

The specific behaviors of probes 1336 and 1337 are dependent to a significant extent on the assay format in which they are employed. Conversely, the assay format will dictate certain of the optimal design features of particular probes. The "essence" of the probes of the invention is not to be construed as restricted to the specific string of nucleotides in the probes named 1336 and 1337. For example, the length of these particular oligonucleotides was optimized for use in the dot blot assay (and certain other anticipated assays) described below. It is well known to one skilled in the art that optimal probe length will be a function of the stringency of the hybridization conditions chosen and hence the length of the instant probes may be altered in accordance therewith. Also, in considering sets comprised of more than one probe, it is desirable that all probes behave in a compatible manner in any particular format in which they are both employed. Thus, the exact length of a particular probe will to a certain extent reflect its specific intended use.

The "essence" of the probes described herein resides in the discovery and utilization of the *Staphylococcus aureus* specific sequences described above and given in Table 1 (core variation).

Hybridization Analysis of Probe Behavior

The sequence data in Table 1 suggest that probes 1336 and 1337 should hybridize to a significant number of *Staphylococcus aureus* strains. The 23S rRNAs of the *Staphylococcus aureus* strains and cistron whose sequences have been inspected all are identical through the target region shown in Table 1. However, this is a small collection of *Staphylococcus aureus* strains compared to the number of known isolates. Potentially, much greater sequence variation might exist in other *Staphylococcus aureus* strains not inspected by sequence analysis. Such variation might reduce or conceivably eliminate hybridization. Therefore, carefully documenting the hybridization behavior to *Staphylococcus aureus* isolates is preferred in order to maintain confidence regarding the probes specificity.

Equally as important as the inclusivity behavior of the probes, is their exclusivity behavior, i.e., their reactivity toward non-*Staphylococcus aureus* bacteria. The number and types of non-*Staphylococcus aureus* strains which might be encountered in a potentially *Staphylococcus aureus* containing test sample are extremely large. The selected sequences shown in Table 1 all are close relatives of *Staphylococcus aureus*, especially *S. epidermidis* and *S.*

*carnosis*, and might be expected to have rRNA sequences highly similar to that of *Staphylococcus aureus*. In fact, extensive and careful inspection of the 16S rRNAs of these and other bacteria has so far turned up no regions useful for discriminating between *Staphylococcus aureus* and other Staphylococcus species. The discovery of a small stretch of conserved sequence variation between the 23S rRNAs of *Staphylococcus aureus* and *Staphylococcus epidermidis* (indicated as the core region of variation in Table 1) therefore was unanticipated and unexpected. However, as discussed above, these patterns of sequence difference might not hold for every strain of *Staphylococcus epidermidis* or other Staphylococcus stains.

Therefore, the behavior of the probes toward representative *Staphylococcus aureus* and non-*Staphylococcus aureus* bacteria was determined by hybridization analysis using a dot blot procedure.

EXAMPLE 1

Dot Blot Analysis of Probe Hybridization Behavior

Dot blot analysis, in accordance with well known procedures, involves immobilizing a nucleic acid or a population of nucleic acids on a filter such as nitrocellulose, nylon, or other derivatized membranes which readily can be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target sequence will exhibit a higher level of hybridization than probes containing less complementarity. For the oligonucleotide probes described herein, hybridization to rRNA targets at 60° C. for 14–16 hours (in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine), followed by three 15 minute post-hybridization washes at 60° C. (in 0.03M NaCl, 0.004 M Tris-HCl, pH 7.8, 0.2 mM EDTA, and 0.1% SDS) to remove unbound probes, would be sufficiently stringent to produce the levels of specificity demonstrated in Table 2.

Techniques also are available in which DNA or RNA present in crude (unpurified) cell lysates can be immobilized without first having to purify the nucleic acid in question (e.g. Maniatis, T., Fritsch, E. F. and Sambrook, J., 1982, Molecular Cloning:A Laboratory Manual). This latter approach was found to significantly decrease the amount of effort required to screen for particular nucleotide sequences which may be present in the nucleic acids of any particular organism and, moreover, is advantageously amenable to the mass screening of large numbers of organisms.

Most of the data shown in Table 2 was produced by hybridization of the indicated probes to purified RNA preparations from the indicated Staphylococcus and non-Staphylococcus bacteria. In addition, crude bacterial lysates of some 72 clinical and 11 veterinary isolates of *Staphylococcus aureus* (as indicated in Table 2) also were tested. Both methods yielded essentially equivalent results. In both cases the probes were end labeled with radioactive phosphorous 32, using standard procedures. Following hybridization and washing as described above, the hybridization filters were exposed to X-ray film and the intensity of the signal "scored" with respect to control spots of known amount of target material (cells or RNA) visually.

As indicated in Table 2, some 92 strains/isolates of *Staphylococcus aureus* have been tested. A small but representative sampling of 9 stains, isolated from different clinical sources, was obtained from the American Type Culture Collection (ATCC). The rest (72) were random isolates from the culture collections and patient populations of major hospitals and diagnostic laboratories in the Massachusetts area including: Massachusetts State Laboratory, Framingham Union Hospital, Brigham and Women's Hospital, and Tufts Veterinary Diagnostic Laboratory.

All *S. aureus* strains hybridize strongly to both probes 1336 and 1337. (++++ signal indicates hybridization signal equivalent to that of the "control" *Staphylococcus aureus* for which a perfect match between probe and target sequences has been explicitly determined by sequence analysis.) Therefore, the inclusivity behavior of the probes can be predicted to be quite good.

In terms of exclusivity (i.e., hybridization to non-*Staphylococcus aureus*) the two probes each behave differently. Some 87 non-Staphylococcus strains, representing 15 species; and 41 non-Staphylococcus bacteria, representing 34 species of 14 genera, were tested (Table 2). Probe 1337 appears to have perfect exclusivity. That is, only barely detectable hybridization, to only a few non-aureus Staphylococci, is observed. (+ signal indicates hybridization signal barely detectable even after prolonged, overnight exposure of the autoradiograph.) Therefore, probe 1337 is both highly inclusive for and highly specific to *Staphylococcus aureus* bacteria. In single probe assay formats, probe 1337 would be the preferred probe.

Probe 1336 has somewhat broader inclusivity than probe 1337. In addition to hybridizing to all *Staphylococcus aureus* stains tested, it hybridizes to strains of a number of other Staphylococcus species. In particular, probe 1336 hybridizes strongly to *Staphylococcus capitis*, and *Staphylococcus xylosus*, most strains of *Staphylococcus epidermidis* and *Staphylococcus saprophyticus*, and some strains of *Staphylococcus hominis*. It also hybridizes weakly, (++ signal defined as very faint compared to control levels but distinct even after four hour exposures of the autoradiograph) to some strains of *Staphylococcus haemolyticus* and *Staphylococcus warneri*. These represent the Staphylococcus species most closely related to *Staphylococcus aureus* by DNA/DNA hybridization (Kloos, W. E, and Schleifer, K. H, 1986, in Bergey's Manual of Systematic Bacteriology, vol. 2, p. 1013–1035). However, probe 1336 does not hybridize to all Staphylococcus species (*S. auricularis, S. caseolyticus, S. cohnii, S. intermedius, S. lentus, S. sciuri,* and *S. simulans* are not detected), nor does it hybridize to any non-Staphylococcus bacteria on the panel shown in Table 2. Therefore, probe 1336 has the useful property of being, in its own right, a "higher-level" Staphylococcus probe of as yet undetermined significance. Its hybridization behavior clearly implies the nature of the nucleotide sequence in 23S rRNA (target) regions of these Staphylococcus strains and, therefore, also implies their taxonomic (systematic) clustering at the sub-genus level. This taxonomic pattern has not been observed previously.

As discussed above, probe 1336 also has significant value as a companion probe to probe 1337 for use in any of a variety of dual probe, sandwich-type hybridization assay formats (e.g. the homopolymer capture, dual probe, liquid hybridization format described in U.S. Ser. Nos. 277,579; 169,646, or 233,683). In such an application, probe 1337 or a derivative would be modified at its 3' terminus to contain a tract of deoxyadenosine (dA) residues ca. 20–200 residues long. This would be used to "capture" the target rRNA (following liquid hybridization) from the test sample onto a solid support (e.g., beads, plastic surface, filter, etc.) which had been suitably derivatized with polydeoxythymidine (dT) for this purpose. Probe 1336 would be used as the detection probe and would be derivatized by some detectable ligand (e.g. 32-P, fluorescien, biotin, etc.). The modified cytosine residues indicated in Table 1 are useful as a convenient means of attaching such a ligand. Detection of the presence of the target nucleic acid in a test sample then is indicated by the capture of the detection ligand onto the solid surface through the series of hybridization interactions:

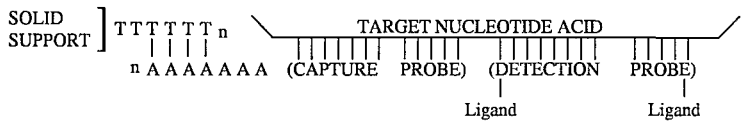

This could occur only if the target nucleic acid is present in the test sample.

The physical properties which make probes 1336 and 1337 useful as a probe set are: 1) Their combined hybridization properties, and 2) their physical proximity to one another. This latter characteristic minimizes the chance that ribonuclease present in some test samples might negatively impact the test result by severing the target rRNA molecule between the target sites of the capture and detection probes—thus artificially (and falsely) severing the link which holds the above-described, molecular sandwich together.

The useful combined hybridization properties includes the following observations.

1) probe 1336 does hybridize to all *Staphylococcus aureus* tested and so, used as a detection probe, would detect all *S. aureus* target nucleic acids "captured" by its companion probe, probe 1337 (i.e. the pair of probes would have full inclusivity for *S. aureus*).

2) although probe 1336 does hybridize to a significant number of non-aureus staphylococci, these would not be detected by the pair of probes because probe 1337 would not capture those targets. In this sense a detection probe could, in principle, hybridize to any bacteria at all, as long as it hybridizes to all *S. aureus*—it would simply be a "generic" labeling reagent. The fact that probe 1336 hybridizes only to a few Staphylococcus species other than *S. aureus* and to no non-Staphylococcus bacteria at all imparts an additional practical utility to the pair of probes in that, except for the few non-aureus Staphylococcus species to which probe 1336 hybridizes, both probes of the pair are fully specific for *Staphylococcus aureus*. Therefore, two specific hybridization events, rather than one, are required to detect a positive assay signal.

Other preferred probes of the present invention comprise probes 1336 and 1337 modified by end capping the probes to improve their resistance to degradation.

The preparation of the blocked probes can be accomplished by modifying the published methods which are used to synthesize oligonucleotides (S. L. Beaucage and M. H. Caruthers, 1981, Tetrahedron Letters 22, 1859–1862; S. Agrawal, C. Christodoulous and M. Gait, 1986, Nucleic Acids Research 14, 6227–6245; J. M. Coull, H. L. Weith and R. Bischoff, 1986, Tetrahedron Letters 27, 3991–3994). These modifications ideally incorporate any of a variety of non-nucleoside phosphormidites which can be advantageously attached to the 3' and/or 5' hydroxyl groups of synthetic DNA chains. Since these reagents effectively block one or both of the terminal hydroxyl groups, the resulting synthetic oligonucleotide is resistant to exonuclease digestion.

Examples of reagents which can be used in this application include, but are not limited to, the 5' amino-modifiers available from Glen Research Corporation (Herndon, Va.) and Clontech (Palo Alto, Calif.). Blocking of the oligonucleotides is accomplished by adding the non-nucleoside phosphormidites to the appropriate end or ends of the synthetic oligonucleotide. Generally, the amino-modifier is dissolved in dry acetonitrile or dichloromethane to a final concentration of 0.1M. The resulting solution is then placed onto an appropriate port of an automated DNA synthesizer. All of the necessary synthesis operations such as coupling, oxidizing and deblocking of the blocking reagent are then conducted as described in instrument operations manuals such as those which are provided by Applied Biosystems (Foster City, Calif.) or Biosearch (San Rafel, Calif.).

While the description of the invention has been made with reference to detecting rRNA, it will be readily understood that the probes described herein and probes complementary to those described herein also will be useful for the detection of the genes which specify the rRNA (rDNA) and, accordingly, such probes are to be deemed equivalents to the described probes and encompassed within the spirit and scope to the present invention and the appended claims.

TABLE 1

ALIGNMENT OF PROBE AND TARGET SEQUENCES

| Position # | 274 | 301 304 | 335 |
|---|---|---|---|
| Escherichia coli | 5'-CCUGAAUCAGUGUGUGUGUUAGUGGAA | GCG-UCUGGAAAGG- | CGCGCGAUACAGGGUGACAGCCC |
| Probe 1336 | | | Tc-AGACCTTTCT-ACTTAGTTTCTTTCCATTATTAGc |
| Probe 1337 | CTCAATGTTTCCTGCTGTAATCTGCTTA-5' | | |
| *Staphylococcus aureus* 1 | GAGUUACAAAGGACGACAUUAGACGAAUCA- | UCUGGAAAGA-UGAAUCAAAGAAGGUAAAUWAUCC | |
| *Staphylococcus aureus* 2 | GAGUUACAAAGGACGACAUUAGACGAAUCA- | UCUGGAAAGA-UGAAUCAAAGAAGGUAAUAAUCC | |
| *Staphylococcus aureus* 3 | GAGUUACAAAGGACGACAUUAGACGAAUCA- | UCUGGAAAGA-UGAAUCAAAGAAGGUAAAUAAUCC | |
| *Staphylococcus aureus* 4 | GAGUUACAAAGGACGACAUUAGACGAAUCA- | UCUGGAAAGA-UGAAUCAAAGAAGGUAAUAAUCC | |
| *Staphylococcus aureus* 5 | GAGUUACAAAGGACGACAUUAGACGAAUCA- | UCUGGAAAGA-UGAAUCAAAGAAGGUAAAUAAUCC | |
| core variation (probe 1337) | Gg a CGa CA | | |
| *Staphylococcus epidermidis* | GAGUUACAAAAGAACAUGUUAGACGAAUCA- | UCUKGAAAGA-UKAAUCAAAGAAGGUAAAUWAUCC | |
| core variation (probe 1336) | | Ucuggaaag A-ugAa Uca Aagaaggua aUa A | |
| *Staphylococcus carnosis* | GAGUUACAAAAGAAUCGAUUAGACGAAUCGAACCGUACCUGGAAAGU- | UGGACCCAGAGAAGGAAGGUAAAAGUCC | |
| *Bacillus subtilis* | GAGUUACAAAAGAAUCGAACGAGGUAGAACGAACCUGGAAAGGGCCCCGCCAUAGGAGGUAACAGCCC | | |
| *Bacillus stearothermophilus* | GAGUUACAAAAGAAGGAACGGGGUAGACGAACCGGUCUGGAAAGG-CCGGCCAGAGAAGGUGACAGCCC | | |
| *Listeria monocytogenes* | GAGUUACAAAAGAAAGUUAUAAAAUGAAGCGGUCGGUCUGGAAAGG-CCCGCCAAAGACGGUAACAGCCC | | |
| *Heliobacillus chlorum* | GAGUGA-----AUCAUCCUAGUCGAAGCGGUCGGUCUGGAAAGG-CCCGGCACGCAGGUAACACCCC | | |
| *Micrococcus luteus* | CAGUGA-GGUGCGGGCAUAUAGACGAACCAGUGGAUGCU-GGACCG-UAGAGGGUGAGAGUCC | | |

*Staphylococcus aureus* 1 = ATCC 27660 (direct rRNA sequence); 2, 3, 4 = ATCC12600 (rRNA gene sequences from 3 different cistrons); 5 = ATCC12600 (direct rRNA sequence). A = Adenosine, C = cytosine, G = guanidine, T = thymidine, U = uracil, W = A or U, K = G or U, - - = no nucleotide present at that position.

TABLE 2

DOT BLOT HYBRIDIZATION

| Strain | Genus species | Probe 1336 | Probe 1337 |
|---|---|---|---|
| ATCC12600 | Staphylococcus aureus | ++++ | ++++ |
| ATCC25953 | Staphylococcus aureus | ++++ | ++++ |
| ATCC8095 | Staphylococcus aureus | ++++ | ++++ |
| ATCC12598 | Staphylococcus aureus | ++++ | ++++ |
| ATCC13565 | Staphylococcus aureus | ++++ | ++++ |
| ATCC27154 | Staphylococcus aureus | ++++ | ++++ |
| ATCC27659 | Staphylococcus aureus | +++ | ++++ |
| ATCC27660 | Staphylococcus aureus | ++++ | ++++ |
| ATCC27690 | Staphylococcus aureus | ++++ | ++++ |
| Isolates (93 total, see text) | | | |
| Clinical (72) | Staphylococcus aureus | ++++ | ++++ |
| Other (11) | Staphylococcus aureus | ++++ | ++++ |
| GT1930 | Staphylococcus auricularis | – | – |
| GT1935 | Staphylococcus capitis | ++++ | + |
| GT1945 | Staphylococcus caseolyticus | – | – |
| ATCC29974 | Staphylococcus cohnii | – | – |
| GT2052 | Staphylococcus cohnii | – | – |
| ATCC14990 | Staphylococcus epidermidis | ++++ | – |
| GT402 | Staphylococcus epidermidis | ++++ | + |
| GT403 | Staphylococcus epidermidis | ++++ | + |
| ATCC155 | Staphylococcus epidermidis | ++ | – |
| ATCC29885 | Staphylococcus epidermidis | + | – |
| ATCC17917 | Staphylococcus epidermidis | + | – |
| GT2053 | Staphylococcus epidermidis | ++++ | – |
| GT2085 | Staphylococcus epidermidis | ++++ | – |
| GT2086 | Staphylococcus epidermidis | ++++ | – |
| GT2087 | Staphylococcus epidermidis | ++++ | – |
| GT2088 | Staphylococcus epidermidis | ++++ | – |
| GT2097 | Staphylococcus epidermidis | ++++ | – |
| GT2204 | Staphylococcus epidermidis | +++ | – |
| GT2205 | Staphylococcus epidermidis | ++++ | – |
| GT2254 | Staphylococcus epidermidis | ++++ | – |
| GT2255 | Staphylococcus epidermidis | +++ | – |
| GT2256 | Staphylococcus epidermidis | +++ | – |
| GT2257 | Staphylococcus epidermidis | +++ | – |
| GT2294 | Staphylococcus epidermidis | ++++ | – |
| GT2258 | Staphylococcus epidermidis | +++ | – |
| GT2295 | Staphylococcus epidermidis | +++ | – |
| GT2296 | Staphylococcus epidermidis | ++++ | – |
| GT2297 | Staphylococcus epidermidis | +++ | – |
| GT2296 | Staphylococcus epidermidis | +++ | – |
| GT2299 | Staphylococcus epidermidis | +++ | – |
| GT2300 | Staphylococcus epidermidis | ++++ | – |
| GT2318 | Staphylococcus epidermidis | ++++ | – |
| GT2319 | Staphylococcus epidermidis | ++ | – |
| GT2320 | Staphylococcus epidermidis | ++++ | – |
| GT2349 | Staphylococcus epidermidis | +++ | – |
| GT1162 | Staphylococcus haemolyticus | – | – |
| ATCC29970 | Staphylococcus haemolyticus | ++ | – |
| GT2089 | Staphylococcus haemolyticus | – | – |
| GT2222 | Staphylococcus haemolyticus | + | – |
| GT2292 | Staphylococcus haemolyticus | ++ | – |
| GT2317 | Staphylococcus haemolyticus | ++ | – |
| ATCC27844 | Staphylococcus hominis | ++ | – |
| GT1752 | Staphylococcus hominis | ++++ | + |
| GT1875 | Staphylococcus hominis | ++++ | – |
| GT400 | Staphylococcus hominis | ++++ | – |
| GT2051 | Staphylococcus hominis | – | – |
| GT2090 | Staphylococcus hominis | – | – |
| GT2321 | Staphylococcus hominis | ++++ | – |
| ATCC29663 | Staphylococcus intermedius | – | – |
| GT2091 | Staphylococcus intermedius | – | – |
| GT2098 | Staphylococcus intermedius | – | – |
| GT2099 | Staphylococcus intermedius | – | – |
| GT2100 | Staphylococcus intermedius | – | – |
| GT2096 | Staphylococcus intermedius | – | – |
| GT2148 | Staphylococcus intermedius | – | – |
| GT2149 | Staphylococcus intermedius | – | – |
| GT2150 | Staphylococcus intermedius | – | – |
| GT2151 | Staphylococcus intermedius | – | – |
| GT2152 | Staphylococcus intermedius | – | – |
| GT2153 | Staphylococcus intermedius | – | – |
| GT2154 | Staphylococcus intermedius | – | – |
| GT2206 | Staphylococcus intermedius | – | – |
| GT2207 | Staphylococcus intermedius | – | – |
| GT2213 | Staphylococcus intermedius | – | – |
| ATCC29070 | Staphylococcus lentus | – | – |
| GT2266 | Staphylococcus saprophyticus | ++++ | – |
| ATCC15303 | Staphylococcus saprophyticus | ++++ | – |
| GT1808 | Staphylococcus saprophyticus | ++++ | – |
| GT1809 | Staphylococcus saprophyticus | ++++ | – |
| GT1810 | Staphylococcus saprophyticus | ++++ | – |
| GT1876 | Staphylococcus saprophyticus | ++++ | – |
| GT1931 | Staphylococcus saprophyticus | ++++ | – |
| GT2031 | Staphylococcus saprophyticus | ++++ | – |
| GT2049 | Staphylococcus saprophyticus | ++++ | – |
| GT2048 | Staphylococcus saprophyticus | – | – |
| GT2050 | Staphylococcus saprophyticus | ++++ | – |
| ATCC29060 | Staphylococcus sciuri | – | – |
| ATCC29062 | Staphylococcus sciuri | – | – |
| ATCC27848 | Staphylococcus simulans | – | – |
| GT2092 | Staphylococcus simulans | – | – |
| GT2259 | Staphylococcus simulans | – | – |
| GT2260 | Staphylococcus simulans | – | – |
| GT2316 | Staphylococcus simulans | – | – |
| ATCC27836 | Staphylococcus warneri | ++ | – |
| GT2093 | Staphylococcus warneri | – | – |
| GT2293 | Staphylococcus warneri | + | – |
| ATCC29971 | Staphylococcus xylosus | ++++ | – |
| GT803 | Bacillus brevis | – | – |
| GT00B | Bacillus cereus | – | – |
| GT811 | Bacillus coagulans | – | – |
| GTBO4 | Bacillus subtilis | – | – |
| IG3224 | Citrobacter freundii | – | – |
| IG3240 | Citrobacter freundii | – | – |
| 3613-63 | Citrobacter diversus | – | – |
| GTS0049 | Enterobacter agglomerans | – | – |
| 124(lt.pnk.) | Enterobacter cloacae | – | – |
| 41Y | Klebsiella oxytoca | – | – |
| ATCC33403 | Kurthia zopfii | – | – |
| GT256 | Lactobacillus acidophilus | – | – |
| IG3191 | Listeria monocytogenes | – | – |
| IG3299 | Listeria monocytogenes | – | – |
| ATCC401 | Micrococcus conglomeratus | – | – |
| ATCC381 | Micrococcus luteus | – | – |
| ATCC186 | Micrococcus roseus | – | – |
| GT298 | Micrococcus sp. | – | – |
| GT299 | Micrococcus sp. | – | – |
| ATCC14404 | Planococcus citreus | – | – |
| ATCC27964 | Planococcus halophilus | – | – |
| ATCC23566 | Salmonella typhimurium | – | – |
| RF755 | Salmonella typhi | – | – |
| RF910 | Salmonella arizonae | – | – |
| RF968 | Shigella sonnei | – | – |
| RF970 | Shigella dysenteriae | – | – |
| RF974 | Shigella boydii C13 | – | – |
| ATCC13881 | Sporosarcina ureae | – | – |
| ATCC6473 | Sporosarcina ureae | – | – |
| GT405 | Streptococcus agalactiae | – | – |
| GT668 | Streptococcus bovis | – | – |
| GT406 | Streptococcus faecalis | – | – |
| GT407 | Streptococcus faecium | – | – |
| 6056 | Streptococcus faecium | – | – |
| DAC | Streptococcus faecium | – | – |
| GT412 | Streptococcus mutans | – | – |
| GT408 | Streptococcus pneumoniae | – | – |
| GT410 | Streptococcus salivarius | – | – |
| GT411 | Streptococcus sanguis | – | – |

What is claimed is:

1. A nucleic acid probe which consists of or is fully complementary to at least 90 percent of a sequence of any 10 or more consecutive nucleotides within a region of the 23S rRNA of *Staphylococcus aureus* bounded by nucleotide positions 274 to 301, and which includes a nucleotide sequence identical or fully complementary to core region GGACGACA, wherein said core region is within said region bounded by nucleotide positions 274 to 301.

2. The nucleic acid probe of claim 1, wherein said probe is probe 1337, or a nucleic acid sequence fully complementary thereto.

3. A method of detecting the presence of *Staphylococcus aureus* in a sample comprising:

contacting the sample with a nucleic acid probe of claim 1;

imposing hybridization conditions on the sample and said nucleic acid probe which allow said probe to hybridize to the rRNA or rDNA of *Staphylococcus aureus,* if present in the sample, to form hybridized nucleic acid complexes, under conditions which do not allow said nucleic acid probe to form stable hybridized nucleic acid complexes with non-*Staphylococcus aureus* rRNA or rDNA; and detecting said complexes as an indication of the presence of *Staphylococcus aureus* in said sample.

4. The method of claim 3, wherein said nucleic acid probe is probe 1337, or a nucleic acid sequence fully complementary thereto.

5. The method of claim 3, wherein the sample is contacted with a set of probes comprising probes 1336 and 1337.

6. An assay kit comprising the nucleic acid probe of claim 1.

7. A set of nucleic acid probes comprising a probe of claim 1 and a probe consisting of or fully complementary to at least 30 consecutive nucleotides within nucleotide sequence AGUCUGGAAAGAUGAAUCAAAGAAGGUAAUAAUCG, and which includes a nucleotide sequence identical or fully complementary to core region UCUGGAAAGAUGAAUCAAAGAAGGUAAUAA, wherein said core region is within said nucleotide sequence.

8. A set of nucleic acid probes of claim 7 comprising probe 1337, or a nucleic acid sequence fully complementary thereto, and probe 1336, or a nucleic acid sequence fully complementary thereto.

9. A probe comprising a nucleic acid probe of claim 1 and one or more of an end cap, a homopolymer nucleotide tail, and a detectable ligand.

10. A nucleic acid probe which consists of or is fully complementary to 30 or more consecutive nucleotides within nucleotide sequence AGUCUGGAAAGAUGAAUCAAAGAAGGUAAUAAUCG, and which includes a nucleotide sequence identical or fully complementary to core region UCUGGAAAGAUGAAUCAAAGAAGGUAAUAA, wherein said core region is within said nucleotide sequence.

11. The nucleic acid probe of claim 10, wherein said probe is probe 1336, or a nucleic acid sequence fully complementary thereto.

12. A method of detecting the presence of Staphylococcus in a sample comprising:

contacting the sample with a nucleic acid probe of claim 10;

imposing hybridization conditions on the sample and said nucleic acid probe which allow said probe to hybridize to the rRNA or rDNA of Staphylococcus, if present in the sample, to form hybridized nucleic acid complexes, under conditions which do not allow said nucleic acid probe to form stable hybridized nucleic acid complexes with non-Staphylococcus rRNA or rDNA; and detecting said complexes as an indication of the presence of Staphylococcus in said sample.

13. The method of claim 12, wherein said nucleic acid probe is probe 1336, or a nucleic acid sequence fully complementary thereto.

14. An assay kit comprising the nucleic acid probe of claim 10.

15. A probe comprising a nucleic acid probe of claim 10 and one or more of an end cap, a homopolymer nucleotide tail, and a detectable ligand.

\* \* \* \* \*